United States Patent [19]

Kifune et al.

[11] Patent Number: 4,932,404
[45] Date of Patent: Jun. 12, 1990

[54] CHITIN FIBERS AND PROCESS FOR THE PRODUCTION OF THE SAME

[75] Inventors: Koji Kifune, Nara; Katsuhiro Inoue; Shigeru Mori, both of Kyoto, all of Japan

[73] Assignee: Unitaka, Ltd., Hyogo, Japan

[21] Appl. No.: 368,952

[22] Filed: Jun. 13, 1989

Related U.S. Application Data

[60] Continuation of Ser. No. 204,975, Jun. 3, 1988, abandoned, which is a continuation of Ser. No. 544,197, Oct. 21, 1983, abandoned, division of Ser. No. 316,384, Oct. 29, 1981, Pat. No. 4,431,601.

[30] Foreign Application Priority Data

Oct. 29, 1980 [JP] Japan .................. 55-152558
Nov. 20, 1980 [JP] Japan .................. 55-164268

[51] Int. Cl.⁵ ............................ A61L 17/00
[52] U.S. Cl. ................................ 606/230
[58] Field of Search ............ 128/335.5, 334 R; 428/375; 536/20, 53; 264/184, 186

[56] References Cited

U.S. PATENT DOCUMENTS

| | | | |
|---|---|---|---|
| 3,371,069 | 2/1968 | Miyamae et al. | 128/335.5 |
| 3,630,205 | 12/1971 | Listner | 128/335.5 |
| 3,988,411 | 10/1976 | Capozza | 536/53 |
| 4,029,727 | 6/1977 | Austin et al. | 264/186 |
| 4,431,601 | 2/1984 | Kifune et al. | 264/186 |

Primary Examiner—C. Fred Rosenbaum
Assistant Examiner—Sharon Rose
Attorney, Agent, or Firm—Sughrue, Mion, Zinn, Macpeak & Seas

[57] ABSTRACT

A fiber comprised of chitin having a single yarn denier of 0.5 to 20 and a dry tensile strength of 2 g/d or more, and a process for the production thereof are described. The use of such chitin fibers permits the production of surgical sutures having high tensile strength and flexibility, and good absorption properties.

12 Claims, 1 Drawing Sheet

CHITIN FIBERS AND PROCESS FOR THE PRODUCTION OF THE SAME

This is a continuation of application Ser. No. 07/204,975 filed June 3, 1988, now abandoned, which is a continuation of application Ser. No. 06/544,197 filed Oct. 21, 1983 now abandoned which is a divisional application of Ser. No. 316,384 filed Oct. 29, 1981, now U.S. Pat. No. 4,431,601.

FIELD OF THE INVENTION

The present invention relates to chitin fibers and a process for the production of the same. More particularly, it is concerned with chitin fibers having high tensile strength and flexibility, suitable particularly for the preparation of absorbable surgical sutures, and a process for the production of the same.

BACKGROUND OF THE INVENTION

Heretofore, as absorbable surgical sutures, cat guts reproduced from the intestines of sheep have long been known and, recently, polyglycolic acid sutures have been developed. Although these materials are now in wide-spread use for surgical operations, they fail to meet all the requirements of absorbable surgical sutures. For example, cat guts have disadvantages in that they are inferior in ease of use, i.e., handling such as sewing and knotting is poor. Furthermore, their adaptability in vivo is poor because an antigen-antibody reaction may easily occur. In addition, the strength of the sutures is reduced because the sutures must be promptly absorbed in vivo. Also, polyglycolic acid sutures have disadvantages in that handling such as sewing and knotting is poor because of their high coefficient of surface friction. Furthermore, it is difficult to store them for a long period of time since they are readily decomposed in air, and in that the resistance to bacteria is poor, resulting in ready decomposition.

Chitin is a polysaccharide comprising poly(N-acetyl-D-glycosamine) and occurs widely in nature. For example, chitin may be found in the hard shell of crustaceans. Since chitin contains one aminoacetyl group per the recurring unit thereof, it has many interesting and peculiar characteristics. For example, it is absorbed in the tissue after undergoing enzymatic decomposition in vivo, and it has good dyeability. It has therefore been proposed to form chitin into fibers and use them as absorbable surgical sutures. However, absorbable surgical sutures having sufficient performance for practical use have not yet been produced from chitin fibers.

Absorbable surgical sutures must have good adaptability in vivo and be capable of being absorbed in the tissue after holding their tensile strength for a predetermined period of time and being sterilized. In addition, it is required that they have good handling such as ease of sewing and ease of knotting, and have suitable physical properties, such as tensile strength and flexibility, as sutures.

Sutures are usually prepared by twisting a plurality of filaments into threads or strands. In order to enable sutures to have the performance as described above, particularly good handling, i.e., ease of use, and suitable physical properties as sutures, it is necessary that fibers constituting the suture have suitable tensile strength and thickness. In more detail, these fibers are required to have a dry tensile strength of at least 2 g/d and a thickness of 20 denier or less, preferably 0.5 to 20 denier.

Various methods have heretofore been proposed to produce chitin fibers by wet spinning of a chitin solution. However, chitin fibers meeting both the requirements of tensile strength and thickness as described above have not yet been produced.

For example, U.S. Pat. No. 4,029,727 (corresponding to Japanese Patent Application (OPI) No. 133367/1976 (The term "OPI" as used herein refers to a "published unexamined Japanese patent application")) describes chitin dope prepared by dissolving chitin in a trichloroacetic acid-containing solution, wet-spinning and cold-stretching, whereby high tensile strength chitin fibers are obtained. The thus obtained chitin fibers, however, are very thick. It is described in Example 2 that there could be obtained filaments having a tensile strength of 63 kg/mm$^2$. This value corresponds to 5 g/d when calculated assuming that the density is 1.4. Although it is apparent that high tensile strength chitin fibers can be obtained, the diameter thereof is 0.25 mm as shown in Example 3. When calculated with the density as 1.4, this diameter corresponds to 618 denier. Thus, the fibers obtained in U.S. Pat No. 4,029,727 do not meet the requirements as described hereinbefore.

Japanese Patent Application (OPI) No. 127500/1978 describes that chitin was dissolved in a solvent, such as dichloroacetic acid, to prepare a chitin dope solution. The prepared chitin dope solution was set-spun and stretched whereby fine chitin fibers were obtained. The tensile strength of the fiber, however, is low. That is, it is described in the examples that 3.0 to 3.5 denier of chitin fibers were obtained, but that the tensile strength was 1.2 to 1.5 g/d (a knot tensile strength of 0.6 to 0.7 g/d). Thus, it can be seen that the chitin fibers obtained in Japanese Patent Application (OPI) No. 127500/1978 do not meet the requirements as described hereinbefore.

U.S. Pat. No. 3,988,411 describes that chitin was dissolved in hexafluoroisopropyl alcohol or hexafluoroacetone sesquihydride, and the resulting solution was spun to obtain chitin fibers. Sutures are disclosed as being one use of the chitin fiber. However, there is described no chitin fiber is described meeting the foregoing requirements.

The conventional chitin fibers, as described above, fail to meet both the requirements for tensile strength and thickness, that is, the thickness is too large when the tensile strength is sufficient, whereas when the thickness is sufficiently small, the tensile strength is poor. Thus, from such conventional chitin fibers, there cannot be obtained sutures which have suitable physical properties and ease of use, and which are useful for practical use.

Heretofore, chitin fibers having such sufficient tensile strength and flexibility that surgical sutures can be prepared therefrom, i.e., having a suitable thickness, have not yet been known.

SUMMARY OF THE INVENTION

The principal object of the invention is to provide chitin fibers having sufficient tensile strength and flexibility so as to permit the preparation of surgical sutures therefrom, i.e., chitin fibers having a suitable thickness, and, in more detail, chitin fibers having a tensile strength of at least 2 g/d and a thickness of 0.5 to 20 denier.

It has been found that the object can be attained by treating filaments formed in a coagulation bath additionally with a coagulation solution in a free state, and that ideal absorbable surgical sutures can be produced from such chitin fibers.

The present invention, therefore, provides:

(1) a fiber composed of chitin having a single yarn denier of 0.5 to 20 and a dry tensile strength of 2 g/d or more; and (2) a process for producing a fiber, comprising the steps of preparing a dope solution comprised of chitin and a solvent; wet-spinning the dope solution by extruding the dope solution through a nozzle in order to from a filament; coagulating the filament in a coagulating solution, and treating the filament with said coagulating solution wherein the filament is in a state in which substantially no tension is exerted on the filament.

DETAILED DESCRIPTION OF THE INVENTION

Figure 1:
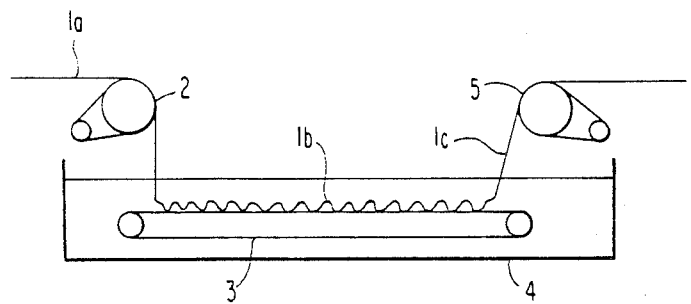
FIGS. 1 and 2 are each an illustrative view of an embodiment of the process of the invention.

The term "chitin" as used herein includes both chitin per se and chitin derivatives. The chitin as used herein can be prepared by subjecting crustaceans and insects to a hydrochloric acid treatment and a caustic soda treatment to thereby separate proteins and calcium, or by additionally applying an etherification treatment, an esterification treatment, etc.

Chitin derivatives as used herein include etherified chitin, e.g., carboxymethylated chitin and hydroxyethylated chitin, and esterified chitin, e.g., acetylated chitin and sulfonated chitin. Esterified chitins include carboxylic acid (e.g., formic acids, acetic acid, butyric acid, valeric acid, isobutyric acid, isovaleric acid, benzoic acid, cinnamic acid, salicylic acid, anthranilic acid, and phthalic acid), sulfonic acids (e.g., sulfuric acid, toluenesulfonic acid, and sulfanyl acid), carbonic acids, and their anhydride esters of chitin. These esterified chitins can be prepared, for example, by treating chitin powder with an acid or aqueous solution thereof as described above. If necessary, as a catalyst, sulfuric acid, hydrochloric acid, toluenesulfonic acid, etc. can be used.

The degree of esterification can be controlled by changing the composition of the treating solution, the temperature, and the treatment time. For example, in the case of acetylation, the treatment can be performed in a relatively short period of time. Acetylated chitin, for example, having a degree of acetylation of about 6% can be prepared by soaking chitin powder in 90% acetic acid at room temperature (20° to 30° C.) for 10 minutes, fully washing with water, neutralizing with ammonium hydroxide, for example, to thereby completely remove free acetic acid, and drying.

The chitin as used herein preferably has a high degree of polymerization. That is, the viscosity at 30° C. of a solution prepared by dissolving 0.2% by weight of chitin in dimethylacetamide containing 10% by weight of lithium chloride (this viscosity is hereinafter referred to as a "solution viscosity") is preferably 300 cps or more, more preferably 500 cps or more, even more preferably 1,000 cps, and most preferably 1,500 cps or more.

The ash content of the chitin as used herein is preferably 2% by weight or less, more preferably 1% by weight or less, even more preferably 0.4% by weight or less, and most preferably 0.1% by weight or less.

Chitin having such a high degree of polymerization and such a small ash content can be prepared by applying a weak acid treatment and an alcohol treatment, or alternatively a weak acid treatment and a ketone treatment as pretreatments in producing purified chitin by subjecting a crude raw material to a dilute acid treatment and a dilute alkali treatment. Weak acids which can be used in the pretreatment include acetic acid, formic acid, propionic acid, citric acid, lactic acid, salicylic acid, tartaric acid, phosphoric acid, carbonic acid, and boric acid, preferably acetic acid. Alcohols which can be used include methanol, ethanol, nypropyl alcohol, and iso-propyl alcohol, preferably methanol and ethanol. Ketones which can be used include acetone, methyl ethyl ketone, and cyclohexane.

In the cases of the weak acid treatment and alcohol treatment as pretreatments in the production of the purified chitin, when the acetic acid is used, the preferred concentration of the acetic acid is 99% by weight, the preferred weight ratio of chitin powder to acetic acid is 1:5 to 1:50, the treatment temperature is preferably 20° to 40° C., and the treatment period is preferably 10 minutes or more, and more preferably 30 minutes or more. After the weak acid treatment, most of the weak acid used is almost all removed by a filtration and then the resulting product is washed with an alcohol, preferably alcohol in the amount of about 50% by weight or more based on the weight of chitin powder, followed by washing with water.

In the case of the dilute acid treatment, for example, when hydrochloric acid having a concentration of 2 normal or less is used, the treatment temperature is preferably 30° C. or less and particularly preferably 15° C. or less, and the treatment period is preferably 5 hours or less and particularly preferably 3 hours or less.

In the case of the dilute alkali treatment, for example, when an aqueous solution of caustic soda having a concentration of 2 normal or less is used, the treatment temperature is preferably 85° C. or less and particularly preferably 75° C. or less, and the treatment period is preferably 5 hours or less and particularly preferably 3 hours or less.

The chitin as used herein is preferred to be in the form of a fine powder and to have a large surface area. The average grain size is preferably 50 mesh or more, more preferably 100 mesh or more, and most preferably 150 mesh or more. The bulk specific gravity under a load of 42 g/cm$^2$, as a measure of the surface area, is preferably 0.4 g/cm$^3$ or less, more preferably 0.35 g/cm$^3$ or less, even more preferably 0.3 g/cm$^3$ or less, and most preferably 0.28 g/cm$^3$ or less. Such chitin powder can be produced by the use of a hammer type grinder or an impact type grinder.

Various known solvents for chitin can be used for the preparation of the chitin dope in solution the invention. Of these known solvents, trichloroacetic acid is preferably used. Since the melting point of trichloroacetic acid is 57° C., it is necessary to maintain trichloroacetic acid at a temperature of at least 57° C. At such temperatures, decomposition of chitin proceeds to a certain extent and, therefore, it is desirable to use an organic solvent in combination, which is capable of dissolving trichloroacetic acid preferably at 50° C. or less and more preferably room temperature (20° to 30° C.) or less.

Solvents which are capable of dissolving trichloroacetic acid and providing a uniform chitin dope at room temperature include chlorinated hydrocarbons. Examples of such chlorinated hydrocarbons are chloromethane, dichloromethane, chloroform, carbon tetrachloride, 1,2-dichloroethane, 1,1,1-trichloroethane, and 1,1,2-trichloroethane. They can be used alone or in combination with each other.

The weight ratio of trichloroacetic acid to chlorinated hydrocarbon is preferably within the range of 25:75 to 75:25. In order to avoid a reduction in the molecular weight of chitin due to decomposition thereof, it is desirable to employ the foregoing range within which the mixed solvent is liquid at room temperature (20° to 30° C.) or less, although the solubility of chitin in the mixed solvent is increased as the trichloroacetic acid content is increased.

The chitin dope solution for use in the practice of the invention can be prepared in the manner described below.

Trichloroacetic acid may be used alone as a solvent, and chitin powder is gradually added to the trichloroacetic acid maintained at a temperature of 57° C. or more to dissolve the chitin therein by stirring. Alternatively, when a mixed solvent of trichloroacetic acid and chlorinated hydrocarbon is used as a solvent, trichloroacetic acid is added to and mixed with chlorinated hydrocarbon at as low a temperature as possible, preferably at 10° C. or less and more preferably 5° C. or less, to prepare a liquid mixed solvent. Chitin powder is gradually added to the thus prepared mixed solvent and dissolved therein by stirring.

The concentration of chitin in the chitin dope solution is preferably 0.5 to 20% by weight, more preferably 0.5 to 10% by weight, and most preferably 1 to 10% by weight. When the concentration of chitin in the chitin dope solution is too high, the dissolution of chitin in the solvent becomes difficult and, furthermore, the production of fibers from such chitin dope solution becomes difficult. On the other hand, when the concentration of chitin is too low, it becomes undesirably difficult to produce fibers having excellent mechanical properties.

The chitin dope solution for use in the invention may contain, if necessary, additives such as a dye, a pigment, a stabilizer, an antioxidant, a heat resistant agent, a germicide, a preservative, an anesthetic, and a filler.

In producing chitin fibers in accordance with the method of the invention, the above prepared chitin dope solution is extruded into a coagulation solution through a nozzle to form filaments containing the solvent. As such coagulation solution, organic ketones, such as acetone, methyl ethyl ketone, methyl isobutyl ketone, diethyl ketone, and cyclopentanone, chlorinated hydrocarbons, such as ethylene chloride, carbon tetrachloride, trichloroethylene, and tetrahydrofuran, hydrocarbons, such as cyclohexane, hexane, and petroleum ether, alcohols, such as methanol, ethanol, isopropyl alcohol, n-butyl alcohol, esters, such as ethyl acetate, amides, such as dimethylformamide and N-methylpyrrolidone, etc., can be used. Of these compounds, anhydrous acetone, anhydrous methanol and anhydrous ethanol are particularly preferred.

The temperature of the coagulation solution is suitably at 10° to 40° C. and particularly suitably at 20° to 35° C. The chitin dope solution is filtered and defoamed, if necessary. Thereafter, it is extruded into the coagulation solution through a nozzle and taken out. For this purpose, the usual wet-spinning apparatus and method can be employed. It is necessary in the invention that the taken out filament is in the state that it contains the solvent, i.e., in an incompletely coagulated state.

The hole diameter of the nozzle for use in the practice of the invention is preferably 0.02 to 0.09 mm, more preferably 0.03 to 0.07 mm, and most preferably 0.04 to 0.06 mm. When the hole diameter is more than 0.09 mm, the tensile strength of the filament tends to decrease, whereas when it is less than 0.02 mm, the spinning operation tends to become difficult, e.g., some particles or dust in the dope solution will close the nozzle. The flow path length (L) in the nozzle section can be determined depending on the hole diameter (D). Usually, it is preferred that the flow path length is determined so that the ratio of the flow path length (L) to the hole diameter (D) (i.e., L/D) be within the range of 1:1 to 10:1. The number of holes in the nozzle is usually 10 to 300 and preferably 20 to 100 although it varies, of course, depending on the desired total denier. Preferred examples of materials of which the nozzle is made are platinum and tantalum.

It is preferred that the chitin dope solution is extruded into the coagulation solution and taken out so that the spinning draft is 0.4 to 1.4. The term "spinning draft" is used in the invention to indicate the ratio of the rate of taking out filaments to the rate of discharging the dope solution through the nozzle. In more detail, it is expressed by the following equation:

$$\text{Spinning Draft} = \frac{\left(\begin{array}{c}\text{Rate of taking out filament}\\\text{(m/minute)}\end{array}\right) \times \left(\begin{array}{c}\text{Hole area of}\\\text{Nozzle (mm}^2\text{)}\end{array}\right)}{\text{Amount of dope solution discharged (ml/minute)}}$$

The spinning draft can be controlled by adjusting the hole diameter of the nozzle, the concentration of chitin in the dope solution, the amount of the dope solution discharged, and the rate of taking out filaments. It is preferred that the hole diameter of the nozzle is adjusted within the range of 0.02 to 0.14 mm, particularly 0.02 to 0.09 mm; the concentration of chitin in the dope solution is within the range of 0.5 to 20% by weight, particularly 1 to 10% by weight; the amount of the dope solution discharged per filament is within the range of 0.003 to 1.7 ml/minute; and that the rate of taking out filaments is within the range of 2 to 50 m/minute. When the spinning draft is more than 1.4, easy breaking of filaments occurs, resulting in a poor spinning operation. On the other hand, when it is less than 0.4, the filament relaxes just after leaving the nozzle and, in extreme cases, the filament comes into contact with the bottom of the coagulation bath in horizontal spinning, resulting in a poor spinning operation.

In controlling the spinning draft, when fibers having high tensile strength are desired, it is preferred that the hole diameter of the nozzle and the rate of taking out filaments are increased, and when fibers having high elongation are desired, it is preferred that the hole diameter of the nozzle and the rate of taking out filaments are reduced. It is preferred from a viewpoint of productivity that the amount of the dope solution discharged is large, the rate of taking out filaments is high, and that the concentration of chitin is high.

In the invention, it is preferred, in view of the spinning operation and the tensile strength of fibers obtained, that the chitin dope solution adjusted to a temperature of 10° C. or less is heated up to 10° C. or more just before coagulation. More preferably, it is heated up to 25° C. or more, even more preferably, it is heated up to 30° C. or more, and most preferably, it is heated up to 35° C. or more. The upper limit of the temperature to which the chitin dope solution can be heated up is generally about 50° C. for the prevention of the reduction in the degree of polymerization of chitin, although it varies depending on the rate of raising the temperature. It is sufficient that the chitin dope solution is heated up to the temperature as described above. The period for which the chitin dope solution is maintained at the foregoing temperature is preferred to be as short as possible in view of the reduction in the degree of polymerization of chitin. The period is usually 1 hour or less, and preferably 30 minutes or less, more preferably 5 minutes or less, and most preferably 1 minute or less.

Any method can be used to raise the temperature of the chitin dope solution to the foregoing level. It is, however, preferred to employ a method in which a transfer tube of the chitin dope solution is heated with electricity, steam, a heating medium or the like, particularly at the areas thereof near the nozzle or die.

In accordance with the method of the invention, the thus formed filament is treated with a coagulation solution in the state that substantially no tension is exerted onto the filament. As described hereinbefore, the taken out filament still contains a part of the solvent. For the treatment of such filaments in the state that substantially no tension is exerted thereon, there can be employed, for example, a method in which the filament taken out by a roller through a coagulation solution (first coagulation bath) after spinning is introduced into a second coagulation bath where it is treated.

Figure 2:
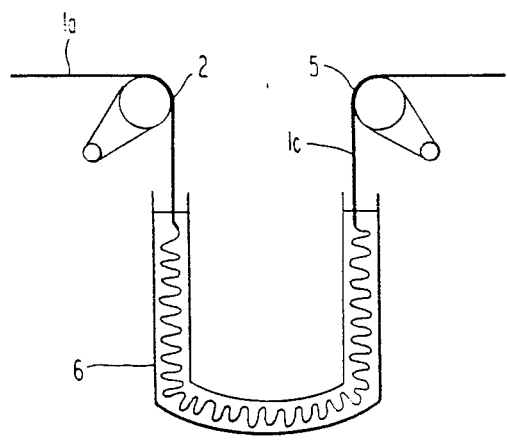

This method is hereinafter described in detail with reference to embodiments thereof as illustrated in FIGS. 1 and 2.

Referring to FIG. 1, a filament 1a taken out by a roller after being extruded into a first coagulation bath through a nozzle is dropped on a conveyor 3 by an introduction roller 2 to thereby form a heap of filament 1b. The conveyor 3 is accommodated in a second coagulation bath 4 and moves at a rate slower than the introduction speed of the filament 1a. The coagulation of the filament further proceeds in the second coagulation bath 4. The heap of filament 1b is again formed into the filament 1c, which is then taken out by the use of a roller 5.

Referring to FIG. 2, a filament 1a which has been extruded into a first coagulation bath through a nozzle and taken out with a roller is dropped by an introduction roller 2 into an apparatus in the form of a curved pipe into which the filament can be packed, e.g., a U-shaped tube 6, and heaped therein. The U-shaped tube 6 is filled with a coagulation solution. The coagulation of the filament further proceeds while it moves toward to the other opening, i.e., outlet of the U-shaped tube 6 by the lamination force. The filament is returned to a filament 1c, which is then taken out with a roller 5.

Any methods or modifications can be used or made as long as the filament can be treated in the state that substantially no tension is exerted thereon. For example, a plurality of second coagulation baths can be provided; the filament introduced into the second coagulation bath can be laminated in the bath as it is introduced into it, thereafter, the filament is taken out; the treatment of the filament can be performed without the provision of the second coagulation bath; the filament leaving the coagulation bath is once wound on, for example, a bobbin or formed into a cake under a tension of 0.5 g/d or less and preferably 0.3 g/d or less and, thereafter, it is treated with a coagulation solution; and so forth.

The coagulation solution used for that purpose may be the same as or different from the coagulation solution used in the first coagulation bath (spinning bath).

It is preferred that the amount of the residual solvent in the filament is within the range of 10 to 50% by weight (based on the weight of the polymer) before the treatment and within the range of 10% by weight or less after the treatment. The treatment time is preferably 1 minute or more and particularly preferably 10 minutes or more. Also, it is preferred to allow the filament to stand overnight or for a longer period of time.

The thus obtained fiber per se has a dry tensile strength of 2 g/d or more. The tensile strength of the fiber can be further increased by stretching. The stretching can be performed either subsequent to the treatment using a coagulation solution, or after neutralization and washing. For this stretching, various known apparatuses can be used. The fiber can be stretched, for example, by about 20 to 80% the original length thereof.

The filament subjected to the treatment using a coagulation solution is, if necessary, neutralized, washed, and dried. For such neutralization, washing and drying, various known apparatuses and methods can be employed.

As described hereinbefore, the method of the invention makes it possible to produce a 0.5 to 20 denier filers of chitin having a dry tensile strength of 2 g/d or more, preferably 2.5 g/d or more, more preferably 3 g/d or more, further preferably 3.5 g/d or more, and still further preferably 4.0 g/d. These chitin fibers are suitable for the production of, in particular, absorbable surgical sutures.

The chitin fiber of the invention is formed into a knitted strand or braid, for example, after application of twisting, to thereby produce all kinds of sutures. The thus produced sutures have the physical properties required for sutures, excellent sewing properties and ease of use, and good adaptability in vivo, i.e., complete absorption in vivo. Thus, they are suitable as absorbable surgical sutures.

A plurality of chitin fibers, for example, 6 to 16 chitin fibers, are twisted or formed in braids whereby sutures can be obtained. The size of the suture can be controlled by changing the thickness of chitin fiber, the number of fibers to be twisted, and the like. According to the standard of collagen sutures by U.S. Pharmacopoeia (called "USP"), USP size 1, 2, 3, 4, 1-0, 2-0, 3-0, 4-0, 5-0, 6-0, 7-0, 8-0, and 9-0 are preferably used.

The knot tensile strength of the thus obtained suture is 1.4 g/d or more, preferably 1.8 g/d or more, more preferably 2.1 g/d or more, further preferably 2.4 g/d or more, and still further preferably 2.8 g/d or more.

These sutures can be treated with, for example, a dye, a pigment, a stabilizer, an antioxidant, a heat resistant agent, a germicide, a preservative, and an anesthetic. Therefore, before the practical use thereof, necessary treatments are applied depending on the purpose for which they are used.

The thus produced sutures have sufficient tensile strength and flexibility as surgical sutures, and furthermore, good sewing and knotting properties due a a low coefficient of the surface friction thereof. They are ideal as absorbable surgical sutures in that they are absorbed in vivo after they hold the necessary strength for about 10 days. More specifically, they have suitable absorption properties in vivo as absorbable sutures, and furthermore they have good resistance against bacteria present inside and outside living bodies. In addition, they have good adaptability in vivo, i.e., an antigen-antibody reaction rarely occurs, and can be easily stored, i.e., decomposition in air hardly occurs.

The chitin fiber of the invention, for example, having a total denier of 30 to 200 can be used as cloth yarn for fabric or special yarn.

The invention is hereinafter described in greater detail with reference to the following examples.

The dry tensile strength was measured under the conditions of a temperature of 25° C. and a relative humidity of 60% by the use of an Instron tensile testor.

The knot tensile strength was determined by measuring the strength of the suture knotted according to the method as defined in USP (881): Tensile Strength-Surgical Suture, under the conditions of a temperature of 25° C. and a relative humidity of 60% by the use of an Instron tensile testor.

EXAMPLE 1 and COMPARATIVE EXAMPLES 1 to 3

The hard shell of Pink Crab (Chione Cepes Opilio-0, fabricus) was fully dried in a hot-air drying chamber maintained at 40° C. and ground by the use of a hammer type grinder while blowing thereinto cold air maintained at 10° C. so that the average grain size was 100 mesh. The thus prepared powder was soaked in 99.5% acetic acid for 30 minutes, filtered, and then fully washed with methanol. Additionally, the powder was treated with 2N HCl at 25° C. for 3 hours, neutralized with caustic potash, washed with water, and subsequently treated with 1N NaOH at 80° C. for 3 hours, neutralized with hydrochloric acid, and washed with water. Thus, white chitin powder was obtained.

The chitin thus obtained had a bulk specific density of 0.26 g/cm$^3$ (under a load of 42 g/cm$^2$), an ash content of 0.4% by weight, and a solution viscosity of 1,035 centipoises.

Thereafter, 3 parts by weight of the chitin powder was dissolved in a mixed solvent consisting of 50 parts by weight of trichloroacetic acid and 50 parts by weight of methylene chloride at 5° C. to prepare a chitin dope solution. The chitin dope solution was a transparent and viscous solution. The chitin dope solution was filtered under a pressure of 4 kg/cm$^2$ by the use of a 1480 mesh stainless steel net, and fully defoamed under reduced pressure.

The thus defoamed chitin dope solution was transferred to a tank, and it was then extruded into acetone (first coagulation bath) maintained at 14° C. under the application of pressure of 2.5 kg/cm$^2$ through a nozzle having a hole diameter of 0.08 mm and 40 holes at a discharge amount of 2.3 ml/min by the use of a gear pump to form filaments. These filaments were taken out at a rate of 10 m/min by the use of a roller. The chitin dope solution leaving the gear pump was introduced in a pipe having diameter of 5 mm $\phi$ and heated at a zone of a length of 10 cm ahead of the nozzle by circulating hot water maintained at 20° C. The temperature of the chitin dope solution leaving the top of the nozzle was 20° C.

The filaments were subsequently introduced into the apparatus shown in FIG. 1 where they were treated in methanol (second coagulation bath) maintained at 15° C. on the conveyor moving at a rate of 0.5 m/min for 5 minutes, and they were then wound on a winder at a rate of 9 m/min. The wound filaments were neutralized by soaking in an aqueous caustic potash solution having a concentration of 0.3 g/l for 1 hour, washed with ion-exchanged water until the pH of the washed water became neutral, dehydrated with a centrifugal dehydrator, and dried under reduced pressure at room temperature overnight to thereby obtain chitin fibers (Sample A). The denier, dry tensile strength and elongation of the chitin fibers were measured, and the results are shown in Table 1.

For comparison, chitin fibers were prepared in the same manner as in Example 1 with the exception that the belt conveyor was not used, and the filaments were merely passed through the second coagulation bath under tension (Sample B). Furthermore, chitin fibers were prepared in the same manner as in Example 1 except that a pair of rollers in parallel with each other were provided in the second coagulation bath in place of the belt conveyor in such a manner that part of the roller was soaked in the second coagulation bath, and the filaments were wound 20 times on the roller and treated under tension (Sample C). Additionally, chitin fibers were prepared in the same manner as in Example 1 except that a nozzle having a hole diameter of 0.15 mm and 3 holes was used in place of the nozzle having a hole diameter of 0.08 mm and 40 holes (Sample D). The performance of each of Samples B, C and D was measured in the same manner as for Sample A, and the results are shown in Table 1.

TABLE 1

| | Sample | Denier (d) Total | Denier (d) Single Yarn | Dry tensile Strength (g/d) | Elongation (%) |
|---|---|---|---|---|---|
| Example 1 | A | 72 | 1.80 | 3.10 | 20.0 |
| Comparative Example 1 | B | 68 | 1.70 | 1.65 | 8.7 |
| Comparative Example 2 | C | 66 | 1.65 | 1.67 | 8.8 |
| Comparative Example 3 | D | 71 | 35.5 | 2.9 | 18.0 |

For each of Samples A, B, C and D, 12 filaments were twisted to form a braid, and a suture of 3-0 according to the standard of USP XX Ed., Collagen Suture (diameter of suture: about 0.32 mm) was produced. The knot tensile strength of the suture was measured, and the results are shown in Table 2.

TABLE 2

| | Sample | Knot Tenacity* (kg) | Knot Tensile Strength (g/d) |
|---|---|---|---|
| Example 1 | A | 1.87 | 1.84 |
| Comparative Example 1 | B | 0.80 | 0.83 |
| Comparative Example 2 | C | 0.79 | 0.84 |
| Comparative Example 3 | D | 1.97 | 1.74 |

*According to the standard of the Japanese Pharmacopoeia (more than 1.25 kg).

Four sutures prepared using Samples A, B, C and D were dyed, sterilized, and used to suture the abdominal muscle of a rabbit. In the case of Samples B and C, breaking frequently occurred during suturing, and it was not possible to complete the suture. Sample D was rigid and was difficult to handle, and could be easily formed into knots. On the other hand, in the case of Sample A, the resistance in muscle during the suture was small, the handling was easy, and the knot was not slippy. Accordingly, the suturing could be performed smoothly. The suture was taken out 5 days, 15 days and 30 days after the deposition, and the knot strength retention ratio thereof was measured. It was 74% in the case of 5 days, 18% in the case of 15 days, and 0% in the case of 30 days. Thus, it showed good absorption properties in vivo.

EXAMPLES 2 to 6

The same chitin dope solution as prepared in Example 1 was filtered and defoamed in the same manner as in Example 1.

The defoamed chitin dope solution was transferred to a tank, and it was then extruded into methanol (first coagulation bath) maintained at 16° C. under a pressure of 2.5 kg/cm$^2$ through a nozzle having a hole diameter of 0.07 mm and 30 holes at a discharge amount of 2.5 ml/min by the use of a gear pump to form filaments. These filaments were taken out at a rate of 15 m/min by the use of a roller, and, subsequently, were accumulated and soaked in methanol (second coagulation bath) containing 0.3 g/l of caustic potash in the free state in which substantially no tension was exerted. The soaked filaments were taken out of the bath 1 minute (Example 2), 10 minutes (Example 3), 1 hour (Example 4), 10 hours (Example 5), and 24 hours (Example 6) after being put into the bath.

The filaments were subsequently neutralized with an aqueous caustic potash solution having a concentration of 0.5 g/l for about 1 hour, repeatedly washed with ion-exchanged water until the washed water became neutral, dehydrated with a centrifugal dehydrator, and dried under reduced pressure at room temperature overnight to prepare four kinds of chitin fibers. The denier, dry tensile strength, and elongation of each of the chitin fibers were measured, and the results are shown in Table 3. All of the fibers of Examples 2 to 6 were silk-like fibers.

Using the thus prepared fibers, sutures were produced in the same manner as in Example 1. The production of sutures was easy, and the sutures thus produced had sufficient tensile strength and knot tensile strength, were flexible and easy in handling, and were satisfactory as surgical sutures.

The knot tensile strength (g/d) of the sutures was 1.41 in the case of Example 2, 1.85 in the case of Example 3, 1.98 in ghe case of Example 4, 1.93 in the case of Example 5, and 2.01 in the case of Example 6.

TABLE 3

| Example | Soaking Time in 2nd Coagulation Bath | Denier (d) Total | Denier (d) Single Yarn | Dry Tensile Strength (g/d) | Elongation (%) |
| --- | --- | --- | --- | --- | --- |
| 2 | 1 min | 64 | 2.13 | 2.25 | 19.2 |
| 3 | 10 min | 61 | 2.03 | 2.98 | 26.9 |
| 4 | 1 hr | 60 | 2.0 | 3.21 | 25.8 |
| 5 | 10 hr | 60 | 2.0 | 3.16 | 28.4 |
| 6 | 24 hr | 59 | 1.96 | 3.20 | 27.3 |

EXAMPLE 7 and COMPARATIVE EXAMPLES 4 and 5

The chitin fiber as prepared in Example 1 was stretched to 1.4 times its original length to obtain a chitin fiber having a denier of 46 (single yarn, 1.16 d), and a dry tensile strength of 4.1 g/d. Thereafter, 12 fibers were twisted to form a braid, and a suture of USP size 4-0 was produced using the braid.

Using the thus produced suture, the back muscle of a rabbit was sutured, and the suture was taken out after a lapse of 5 days, 10 days, 20 days and 30 days. The knot tenacity retention ratio was measured, and at the same time, the tissue reaction in the vicinity of the sutured area was examined.

For comparison, using polyglycolic acid sutures (Comparative Example 4) and cat guts (subjected to the chromic treatment, Comparative Example 5), the same test as above was performed.

The handling of these three kinds of sutures during the suturing was compared. The polyglycolic acid suture was inferior in slipperiness and did not easily enter the tissue. The cat gut was like wire, and it was difficult to seam it to form a knot. On the other hand, the suture of the invention had a silky touch, was easy to handle, entered smoothly into the tissue, and easily formed knots.

The results in respect of absorption properties in vivo are shown in Table 4.

TABLE 4

| | Knot Tenacity (kg) | Knot Tenacity Retention Ratio (%) 5 days | 10 days | 20 days | 30 days | Tissue Reaction near Sutured Area (after 30 days) |
| --- | --- | --- | --- | --- | --- | --- |
| Example 7 | 1.31 | 76 | 52 | 13 | 0 | completely cured |
| Comparative Example 4 | 0.97 | 54 | 32 | 4 | 0 | completely cured |
| Comparative Example 5 | 0.79 | 25 | 12 | 0 | 0 | damage of capillaries in the vicinity of dissolved areas |

As can be readily seen from the results shown in Table 4, in the case of Comparative Examples 4 and 5, the absorption was too rapid, whereas in the case of Example 7, the suture was slowly absorbed for 10 days and, thereafter, was rapidly absorbed, which is desirable for absorbable surgical sutures.

EXAMPLE 8

The hard shell of Pink Crab was dried with hot air maintained at about 50° C. and ground by the use of an impact type grinder while blowing thereinto cold air maintained at 5° C. so that the average grain size was 150 mesh. The thus prepared powder was soaked in 99.5% acetic acid for 30 minutes, filtered, and then fully washed with methanol. Additionally, the powder was treated with 1N HCl at 15° C. for 4 hours, neutralized with caustic soda, and washed with water. It was then treated with 1N NaOH at 80° C. for 3 hours, neutralized with hydrochloric acid, and washed with water. By carrying out this process, white chitin powder was obtained.

The chitin thus obtained had a bulk specific density of 0.24 g/cm$^3$ (under a load of 42 g/cm$^2$), an ash content of 0.05% by weight, and a solution viscosity of 1,580 cps.

The chitin powder was treated in the same manner as in Example 1 except that the amount of the chitin used was changed to 5 parts by weight to thereby prepare a chitin dope. The chitin dope solution was filtered under a pressure of 5 kg/cm$^2$ by the use of a 1480 mesh stainless steel net, and fully defoamed under reduced pressure.

The thus defoamed chitin dope solution was transferred to a tank, and it was extruded into acetone (first coagulation bath) maintained at 30° C. under a pressure of 4 kg/cm$^2$ through a nozzle having a hole diameter of 0.05 mm with 40 holes at a discharge amount of 1.0 ml/min by the use of a gear pump to form filaments.

These filaments were taken out at a rate of 10 m/min by the use of a roller. The chitin dope solution leaving the gear pump was introduced into a 5 mm φ pipe and heated in a zone 10 cm ahead the nozzle by circulating hot water maintained at 35° C. through the jacket zone. The temperature of the chitin dope solution leaving the top of the nozzle was 35° C.

The filaments were treated with methanol in the same manner as in Example 1 except that the treatment time was changed from 5 minutes to 10 minutes. After the treatment, the filaments were stretched to 1.2 times the original length and wound on a winder. The wound filaments were neutralized, washed with water, and dried in the same manner as in Example 1 to thereby obtain chitin fibers. The thus obtained chitin fiber was 42 denier (single yarn denier: 1.05) and the dry tensile strength was 4.35 g/d.

After the filaments were made, 12 filaments were twisted at the number of 400 per inch to prepare a twist. The twist was 4-0 according to the standard of USP XX Ed., Collagen Suture (diameter: 0.2 mm), and the knot tensile strength was 3.1 g/d. The twist had mechanical properties sufficiently usable as a suture, and the surface was smooth and had a soft touch. It exhibited satisfactory performance when used as a suture.

EXAMPLE 9

Using the same chitin dope solution as used in Example 1, filaments were produced in the same manner as in Example 1 and taken out at a rate of 10 m/min by the use of a roller. The filaments were immediately wound under a tension of 0.1 g/d with a pot type winder to thereby form a cake. The cake was soaked in methanol maintained at 15° C. for 1 hour and, thereafter, neutralized, washed, and dried in the same manner as in Example 1 to thereby obtain chitin fibers. The total denier and single yarn denier of the chitin fiber were 69 d and 1.75 d, and the dry tensile strength was 3.15 g/d and the elongation was 19.4%.

Using the above prepared chitin fibers, a suture was produced in the same manner as in Example 1. The suture had a knot tenacity of 1.96 kg and a knot tensile strength of 1.95 g/d. When the suture was subjected to the same suture test as in Example 1, it exhibited excellent performance with respect to ease of handling, suturing properties, and absorption properties in vivo as in the case of Example 1.

While the invention has been described in detail and with reference to specific embodiments thereof, it will be apparent to one skilled in the art that various changes and modifications can be made therein without departing from the spirit and scope thereof.

What is claimed is:

1. A fiber comprised of chitin having a single yarn denier of 0.5 to 20 and a dry tensile strength of 2 g/d or more.

2. A fiber as claimed in claim 1, wherein said dry tensile strength is 2.5 g/d or more.

3. A fiber as claimed in claim 1, wherein said dry tensile strength is 3.5 g/d or more.

4. A fiber as claimed in claim 1, wherein said dry tensile strength is 4 g/d or more.

5. An absorbable surgical suture comprised of a strand or braid formed of a plurality of fibers, wherein each of said fibers is comprised of chitin and has a yarn denier of 0.5 to 20 and dry tensile strength of 2 g/d or more.

6. An absorbable surgical suture as claimed in claim 5, wherein said suture has a knot tensile strength of 1.4 g/d or more.

7. An absorbable surgical suture as claimed in claim 5, wherein said suture has a knot tensile strength of 1.75 g/d or more.

8. An absorbable surgical suture as claimed in claim 5, wherein said suture has a knot tensile strength of 2.1 g/d or more.

9. An absorbable surgical suture as claimed in claim 5, wherein said suture has a knot tensile strength of 2.45 g/d or more.

10. An absorbable surgical suture as claimed in claim 5, wherein said suture has a knot tensile strength of 2.8 g/d or more.

11. A fiber comprised of chitin having a single yarn denier of 0.5 to 20 and dry tensile strength of 3 g/d or more.

12. An absorbable surgical suture comprised of a strand or braid formed of a plurality of fibers, wherein each of said fibers is comprised of chitin and has a yarn denier of 0.5 to 20 and dry tensile strength of 3 g/d or more.

* * * * *